United States Patent
Brown

(10) Patent No.: US 7,092,832 B2
(45) Date of Patent: Aug. 15, 2006

(54) ADAPTIVE COMPENSATION FOR MEASUREMENT DISTORTIONS IN SPECTROSCOPY

(75) Inventor: Christopher D. Brown, Albuquerque, NM (US)

(73) Assignee: InLight Solutions, Inc., Albuquerque, NM (US)

( * ) Notice: Subject to any disclaimer, the term of this patent is extended or adjusted under 35 U.S.C. 154(b) by 0 days.

(21) Appl. No.: 10/733,195

(22) Filed: Dec. 11, 2003

(65) Prior Publication Data

US 2005/0143943 A1    Jun. 30, 2005

(51) Int. Cl.
G01D 18/00    (2006.01)

(52) U.S. Cl. .......................................... 702/85; 702/189

(58) Field of Classification Search ................ 702/85, 702/189–195; 356/302, 303, 451; 600/407, 600/410; 324/307, 308
See application file for complete search history.

(56) References Cited

U.S. PATENT DOCUMENTS

| | | | | |
|---|---|---|---|---|
| 5,291,426 A | * | 3/1994 | Collins et al. | 702/195 |
| 5,435,309 A | * | 7/1995 | Thomas et al. | 600/310 |
| 5,568,400 A | * | 10/1996 | Stark et al. | 702/85 |
| 5,682,152 A | * | 10/1997 | Wang et al. | 341/50 |
| 6,546,378 B1 | * | 4/2003 | Cook | 706/12 |
| 6,580,510 B1 | * | 6/2003 | Nawracala | 356/451 |
| 6,694,020 B1 | * | 2/2004 | Benesty | 379/406.12 |

FOREIGN PATENT DOCUMENTS

| | | | |
|---|---|---|---|
| EP | 658751 A2 | * | 6/1995 |
| EP | 0982583 A1 | | 1/2002 |

OTHER PUBLICATIONS

Berger, Andrew J., et al—"*An Enhanced Algorithm for Linear Multivariate Calibration*" Analytical Chemistry, vol. 70, No. 3, Feb. 1, 1998, pp. 623-627.

Wentzell, Peter D., et al—"*Maximum Likelihood Principal Component Analysis*" Journal of Chemometrics, vol. 11, John Wiley & Sons, Ltd. (1997) pp. 339-366.

Martens, Harald, remarks re R. Sundberg's "Multivariate Calibration" in the Board of the Foundation of the Scandavian Journal of Statistics 1999, pp. 193-196.

Haaland, David M., et al—"*New Prediction-Augmented Classical Least-Squares (PACLS) Methods: Application to Unmodeled Interferents*," Applied Spectroscopy, vol. 54, No. 9, 2000, pp. 1303-1312.

DiFoggio, Rocco, "*Guidelines for Applying Chemometrics to Spectra: Feasibility and Error Propagation,*" Applied Spectroscopy, vol. 54, No. 3, 2000, pp. 94A-113A.

* cited by examiner

*Primary Examiner*—John Barlow
*Assistant Examiner*—Stephen J. Cherry
(74) *Attorney, Agent, or Firm*—V. Gerald Grafe; InLight Solutions, Inc.

(57) ABSTRACT

Methods of reducing the effects of measurement device artifacts on a measurement of a sample are presented. A number of reference measurements performed with the measurement device are observed to identify reference independent components of the reference measurements. The variations of the reference independent components are used as surrogates for possible artifacts of the measurement device. A number of measurements of subjects similar to the sample are observed, and similarity components of the subject measurements that vary in a manner similar to the reference independent components may be identified. The sample measurement is then adjusted to remove at least part of the similarity components that correspond to the variations in the reference independent components. The adjustment of the sample measurement is thereby improved by reducing the effects of artifacts of the measurement device.

22 Claims, 7 Drawing Sheets

ADAPTIVE COMPENSATION FOR MEASUREMENT DISTORTIONS IN SPECTROSCOPY

FIELD OF THE INVENTION

The present invention is related to methods for data capture and analysis. More specifically, the present invention is related to methods for the reduction of measurement errors, and is particularly useful in multivariate analysis of complex measurements such as those in human tissue.

BACKGROUND OF THE INVENTION

As new data collection technologies have evolved, allowing the analysis of more complex signals, techniques for analyzing such data have become more complex. For example, the introduction of new technologies in spectroscopy has allowed the collection of very large amounts of data. In some spectroscopic measurements, a high degree of sensitivity is needed to sense constituents that have relatively low concentrations or that lack highly selective spectral attributes. Devices used in such measurements, however, can capture extraneous signals, which can interfere with the accurate extraction of the desired information. For example, Johnson noise and shot noise, fundamental noise sources present in virtually all optically-based instruments, are often-cited sources of extraneous information. Data capture and analysis techniques can reduce the deleterious effects of such noise sources. For some random noise sources, simply extending measurement times or further optimizing the electronics or instrumental set-up can eliminate noise effects.

There are additional non-fundamental noise sources that can be difficult to model in advance that originate in the measurement device, or in the various interfaces to the device. For example, in infrared or near-infrared Raman spectroscopy, a sample is illuminated using an optical source, and light reflecting from or transmitted through the sample is gathered and analyzed to determine characteristics of the sample. The sensitivity of optical detection elements can change, and the output of the excitation source can change. These are two examples of non-fundamental noise sources. Extending measurement times and co-averaging multiple measurements do not always mitigate non-fundamental noise sources.

One traditional approach to eliminating such artifacts is to make measurements of a reference sample, or background, which ostensibly provides a constant measurement response over time. In some instantiations the reference sample is not a sample at all, but rather a measurement in the absence of any sample, sometimes referred to as a 'blank'. If the measured response of this reference is observed to change, it can be inferred that the character of the instrument response has itself changed. In a common implementation in spectroscopy, a measured spectrum of the background serving as the reference is subtracted from the measured absorbance spectrum of a sample, hypothetically eliminating instrumental or environmental artifacts that have commonly corrupted both the reference and sample measurements. Mathematically, this can be expressed as in equations 1 and 2:

$$x_{samp} = x_{samp}^o + \delta_s \quad (1)$$

$$x_{ref} = x_{ref}^o + \delta_r \quad (2)$$

where $x_{samp}$ is the observed sample spectrum, $x_{ref}$ is the observed reference spectrum, and the superscript 'o' denotes the true (but unobservable) signal character of the sample or reference as indicated. The $\delta$ terms appearing in equations 1 and 2 are the instrumental or environmental noise disturbances distorting the measurements. The correction procedure involving background subtraction (or ratioing when operating in intensity rather than absorbance) entails $$\tilde{x}_{samp} = x_{samp} - x_{ref} \quad (3)$$

Provided the measurement distortions are equivalent, the following relations hold:

$$\tilde{x}_{samp} = (x_{samp}^o + \delta_s) - (x_{ref}^o + \delta_r) \quad (4)$$

$$\tilde{x}_{samp} = x_{samp}^o - x_{ref}^o \quad (5)$$

Thus, the resultant spectrum $\tilde{x}_{samp}$ includes only signal characteristics of the sample and reference, and not distortions in the measurements associated with the measurement device or the sampling environment. There can be aspects of the distortions which do not subtract (e.g., photon shot noise, detector noise), but background subtraction or ratioing does not set out to eliminate these distortions.

In the application of the technique described above it is assumed that $\delta_s = \delta_r$, and that the reference, $x_{ref}^o$, will not vary; hence, any observed change in $\tilde{x}_{samp}$ must be exclusively attributable to a change in the sample. With a collection of background-corrected sample measurements, any number of known multivariate techniques can be used to disassemble the useful signal and, if desired, further determine the sample characteristics of interest. FIG. 1 illustrates this approach result graphically. For instance, a multivariate regression model can be generated from background-corrected spectra to estimate sample properties.

FIG. 2 demonstrates the application of the approach described above when the distortions in the two measurements are non-equivalent, even under scalar multiplication by k:

$$\delta_s \neq k\delta_r \quad (6)$$

If the distortion were simply multiples then conventional background subtraction could still work with trivial modifications. In this case the subtraction of the reference measurement from the sample does not result in the cancellation of the distortion in the sample spectrum.

$$x_{samp} = x_{samp}^o + \delta_s \quad (7)$$

$$x_{ref} = x_{ref}^o + \delta_r \quad (8)$$

The resulting corrected spectrum $\tilde{x}_{samp}$ is still corrupted by the measurement disturbances:

$$\tilde{x}_{samp} = (x_{samp}^o + \delta_s) - (x_{ref}^o + \delta_r) \quad (9)$$

$$\tilde{x}_{samp} = (x_{samp}^o + x_{ref}^o) - (\delta_s + \delta_r) \quad (10)$$

The possible causes of non-equivalence between $\delta_s$ and $\delta_r$ are myriad. Detector non-linearity, and differences in absorption and scattering properties are typical culprits, but there are many others. There is a need for improved techniques for determining accurate measurements in the presence of such distortions.

SUMMARY OF THE INVENTION

The present invention provides a method for adjusting measurements of samples for the measurement distortions such as those introduced by the state of a measurement device, or the environment of the sample or measurement device. Several measurements of a reference sample or samples can be analyzed for aspects or components of variation that are not related to variations in the reference sample or samples. These components of measurement variation are assumed to be related to distortions in the measurement. These distortion-related components of measurement variation can arise from known or unknown causes, and have known or unknown effects on the reference measurements or sample-measuring device measurements. The present invention can use the distortion-related reference component variations in conjunction with several sample measurements to approximate the distortions in the sample measurements, and, if desired, can compensate for the estimated distortions in the sample measurements.

The present invention is applicable in cases where the reference sample does not vary, the reference sample varies in response to the environment or state of the instrument, and where the reference sample varies in a manner which is not dependent on the environment or state of the instrument.

The present invention does not require that the reference measurement distortion and sample measurement distortion be equivalent (or even equivalent within a scalar as per equation 6 above) since the present invention does not rely on direct subtraction of the reference measurement and sample measurement, the usual requirement for background/reference correction as it is routinely employed in current practice. Current practice also is generally not applicable to situations where the reference sample varies in a manner that is not dependent on the environment or state of the instrument. The present invention accordingly is far more flexible, and is applicable in many more situations than the previously-employed subtracting or ratioing methods.

BRIEF DESCRIPTION OF THE DRAWINGS

The drawings, which are not necessarily to scale, depict illustrative embodiments and are not intended to limit the scope of the invention.

DETAILED DESCRIPTION OF THE INVENTION

The following detailed description should be read with reference to the drawings. The drawings depict illustrative embodiments and are not intended to limit the scope of the invention. While the following detailed description is written with reference to a spectroscopic measurement system for quantifying constituents in samples or classifying the samples into categories, the present invention has application to a range of data measurement systems. For example, the present invention can be used with respect to a sonic or magnetic resonance measurement or detection system. Also, the present invention can be used to determine characteristics other than the constitution of a sample, for example, to determine the speed of a moving object, the depth of a body of liquid, or the temperature of an object.

For the purposes of this disclosure, any range or combination of wavelengths of spectral or other data (including, for example, data captured using magnetic resonance, sonic, spatial imaging or other sensing devices) can be encompassed so long as the data can be captured and quantified or categorized. In some embodiments, the measurements can include an electromagnetic spectrum including the ultraviolet, visible, near-infrared or infrared ranges. In some embodiments, measurements of the reference might not be spectroscopic in nature, for example, a measurement may include pressure, temperature, or viscosity. Some embodiments are adapted for use in non-invasive measurement of blood or tissue constituents including, for example, glucose, alcohol, urea, or other blood constituents. Some embodiments are applicable to spectroscopic instrumentation measurements used on-line or at-line for process analytical measurements, and subsequent inference, while other embodiments are applicable to laboratory-based spectrometers. The text herein refers to 'samples', which is not intended to be restrictive. A sample can denote a portion of a whole, and can equally apply to an aliquot of blood, a portion of tissue, or a bucket of grain.

Figure 1:
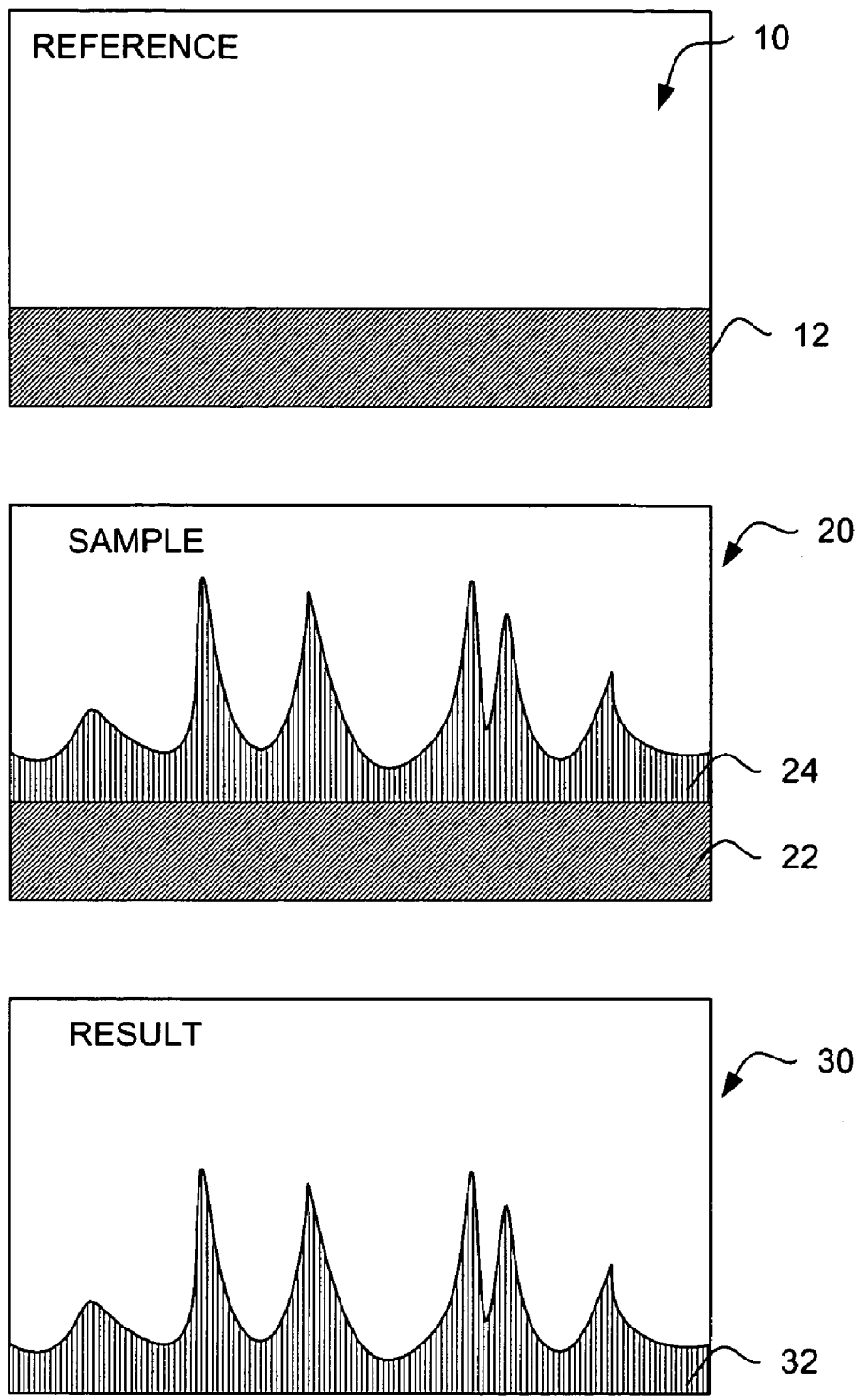
FIG. 1 is a graphical representation of a prior art method of adjusting a measurement.
Figure 2:
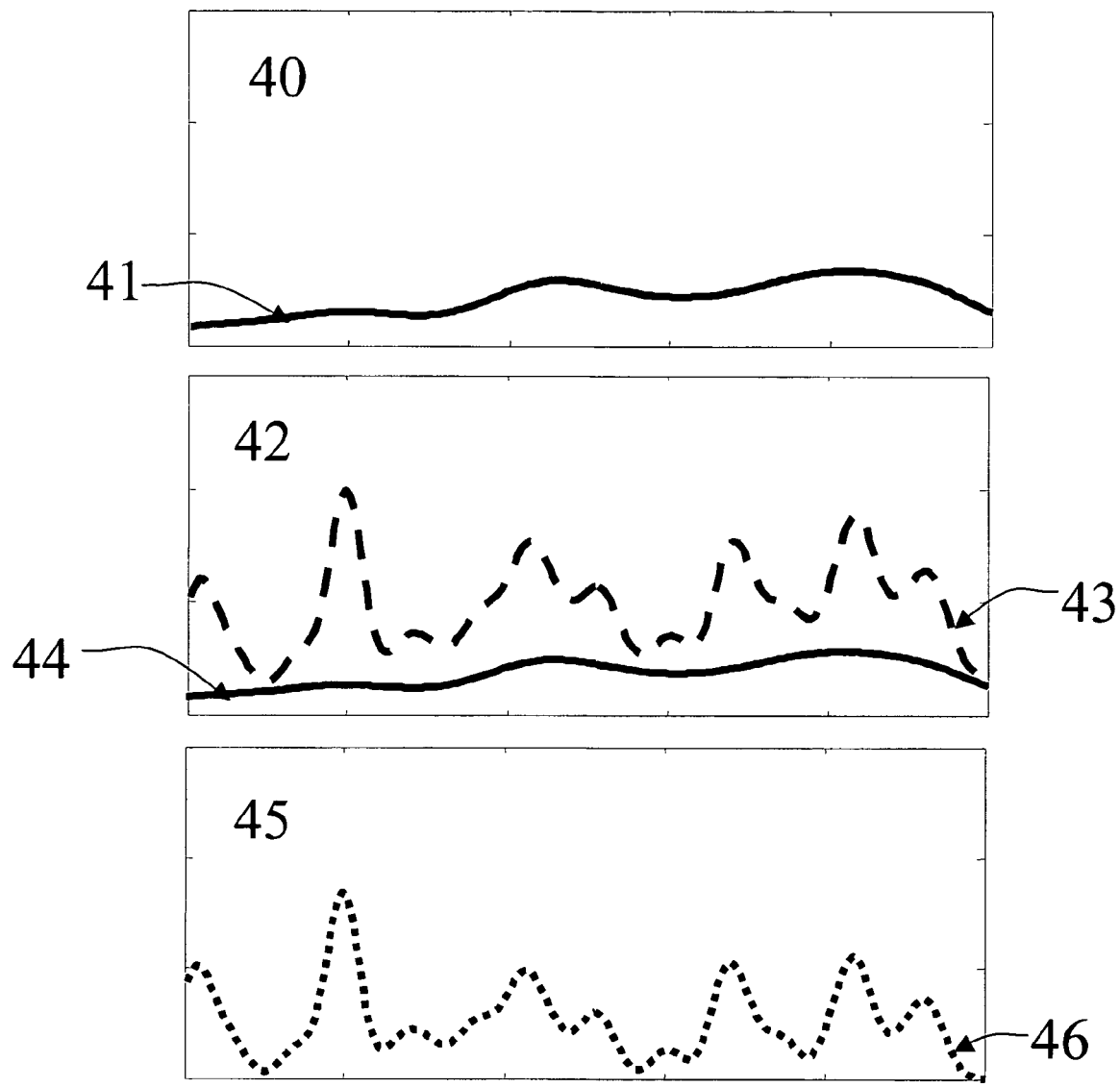
FIG. 2 is an illustration of the application of the method of FIG. 1 to a more complicated spectral system.
Figure 3:
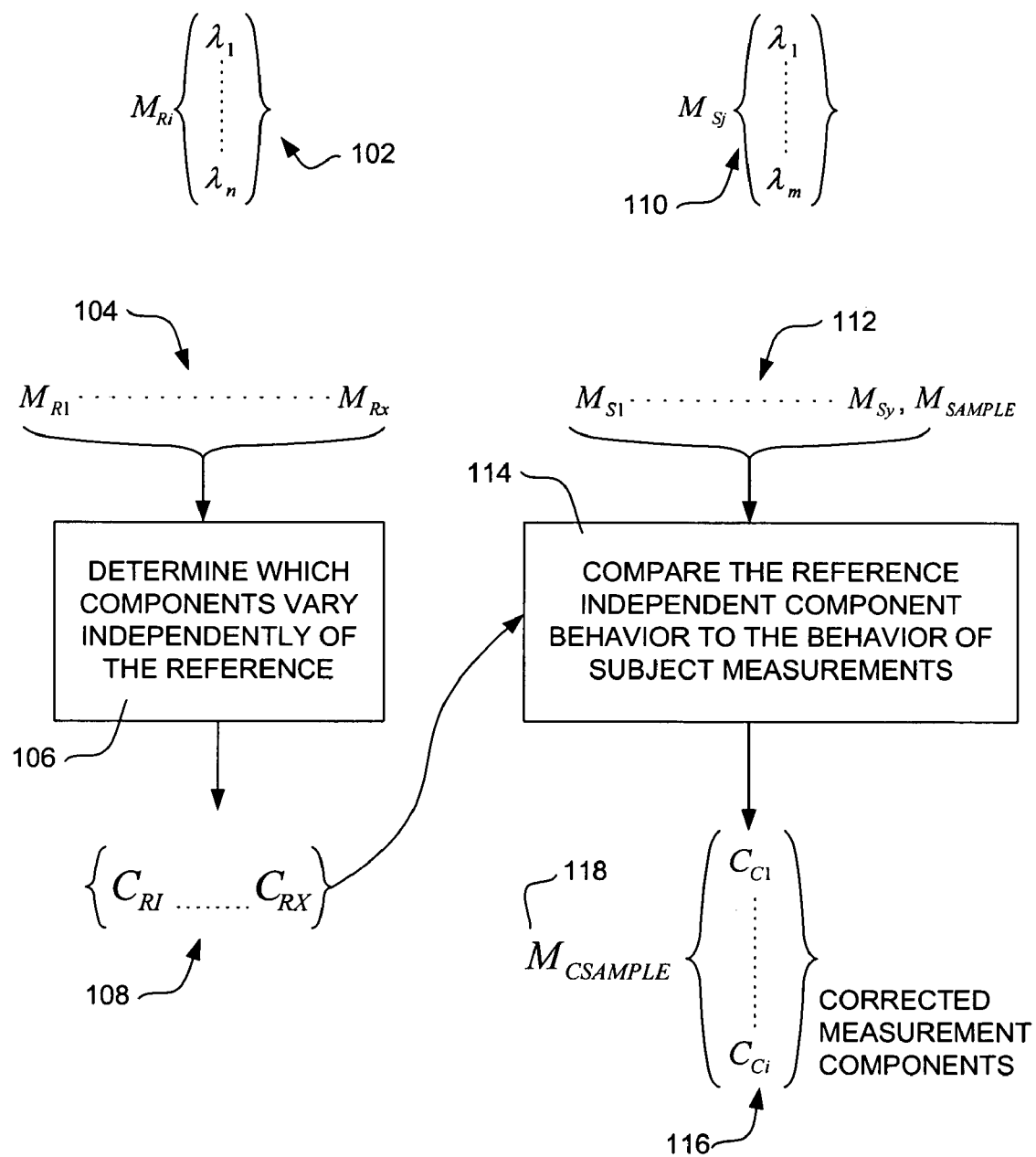
FIG. 3 is an illustration of an example embodiment of the present invention.

FIG. 3 is an illustration of an example embodiment of the present invention. For illustrative purposes, an $i^{th}$ reference measurement 102 is illustrated as including n wavelength channels $\lambda$. A collection of x reference measurements 104 can be retained in a memory or some magnetic or electronic storage (or the like) for comparison purposes. The collection of reference measurements 104 can include one or more reference measurements, which can comprise measurements taken presently, measurements taken at previous times, or a combination thereof. The collection of reference measurements 104 can be organized according to a variety of methods including, for example, sub-organization with respect to the type of reference sample or time of measurement collection. The collection of reference measurements 104 can be analyzed to determine which measurement components vary with and without the reference 106. This can be achieved by using direct or indirect knowledge of the variation pattern of the reference. In other embodiments, the reference can display known or predetermined changes (including not changing at all), or other devices can be used from time to time to determine variations in the reference. The reference measurement components of variation can be functions of the responses at individual wavelengths or channels, or can be functions of combinations of responses at individual wavelengths or channels. In some embodiments, there can be one or more references. Example references can include a number of inert reference samples having distinct, stable characteristics, and a number of reference samples varying differently but whose measurement components vary similarly. For other embodiments, the reference can include some known, modeled, or estimated variation.

With reference-independent components of the measurement variation identified 108, one or more of these components can be further identified as being preferential in characterizing variations relating to environmental or instrumental distortions. This selection can be on the basis of prior information, or other measurable criteria such as the magnitude or frequency of variations.

Each sample measurement 110 contains m wavelength channels $\lambda$. Note that the number of wavelengths captured for the sample measurement 110 need not be the same as that of the reference measurement 102, nor is it necessary that the reference and sample wavelength measurements span the same range. A collection of sample measurements 112 is retained, and like the collection of reference measurements, the collection of sample measurements 112 can comprise any of measurements taken presently and measurements taken at previous times. There is no need for a one-to-one correspondence between the collection of sample measurements 112 and the collection of reference measurements 104 (for example there can be many times more reference measurements than sample measurements), although in some circumstances a one-to-one correspondence can improve the adjustment steps that follow. For resolving distortion-related components of measurement variation related to time, it can be useful if the two collections 104, 112 have some measurements made during similar time frames.

The collection of sample measurements 112 can include a recently acquired sample measurement, Msample 118. In other embodiments, the most recent sample measurement 118 can be excluded from the collection of sample measurements 112, which can allow for faster processing of the sample measurement 118 itself. The collection of sample measurements 112 and the collection of reference-independent measurements 108 are then compared to determine whether any measurement variations in the sample measurements 112 correspond to variations in the reference-independent measurement components 108. To reiterate, any such correspondences need not have a wavelength correspondence, since in this embodiment there is no requirement that the reference measurements are of the same form as the sample measurements. For example, the reference measurements could be electrical resistance measurements, while the sample measurements could be optical absorption in the UV-visible range of the electromagnetic spectrum. Correspondences are then used to create corrected measurement components 116. In an illustrative example, the sample measurement or measurements can be treated to remove or reduce distortions indicated by the correspondence in the reference-independent measurement components of variation 108. Because artifacts can be removed or reduced by observation of correspondences, there is no requirement that any causes of the artifacts be identified or well understood. The corrected measurement components 116 can then be used in making a further measurement of a sample characteristic (e.g., "the creatinine concentration is 1.8 mg/dL"), or qualitative assessment of the sample (e.g., "the blood sample is lipemic").

Figure 4:
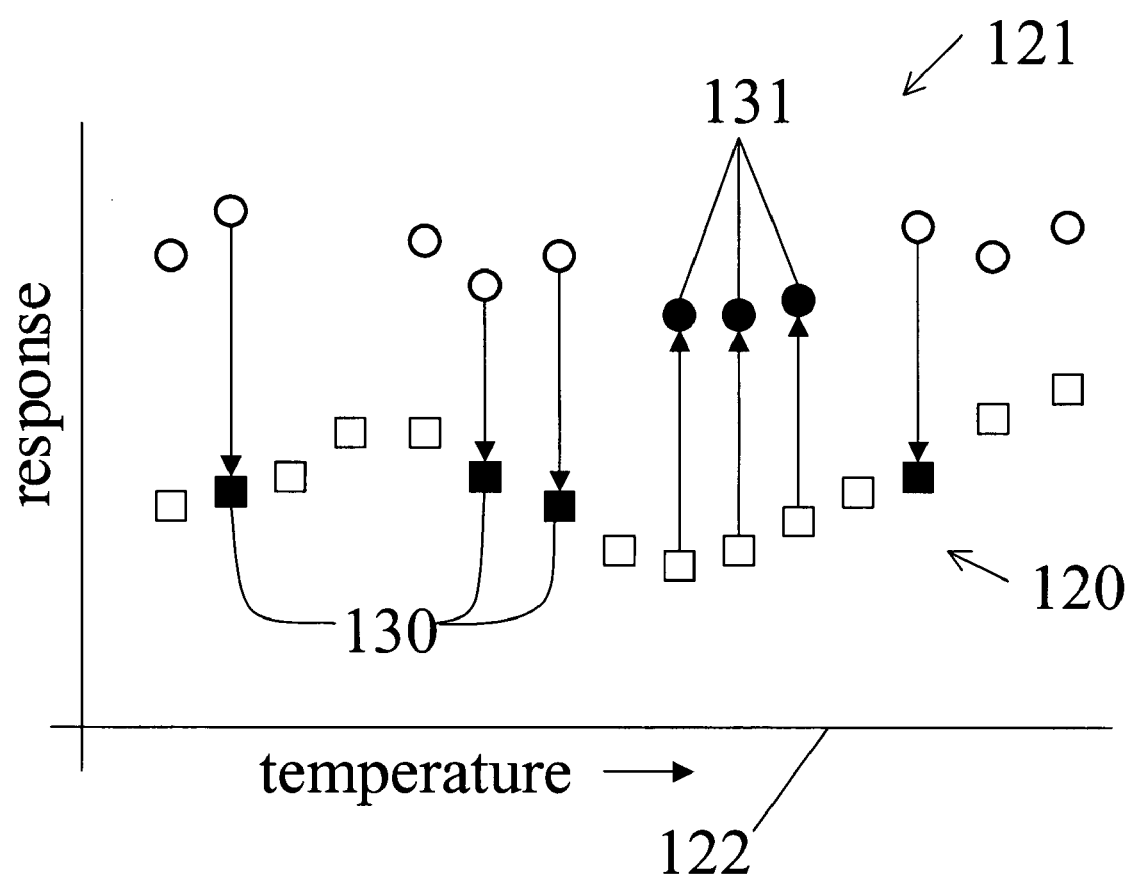
FIG. 4 is an illustration of sample and reference measurements.

In an illustrative example for in-vivo spectroscopy, if several measurements of the tissue of a subject 110 (wherein the subject in some state is akin to the sample discussed above) are taken at about the same time as a single reference measurement 102, analysis to determine similarity of variations of measurement components between the groups of measurements 104, 112 can include analyzing the collection of subject measurements 112 as if only one of the similar-in-time subject measurements 110 was taken to the exclusion of the others, several subject measurements 110 can be combined (e.g., averaged) and treated as a single measurement for the purposes of the comparison 114, or subject measurements matching the reference measurements can be approximated or estimated, for example, by interpolation or extrapolation. It is equally viable that many reference measurements can be acquired at a time similar to a single measurement of the subject state, although similar approaches can be employed. This is illustrated in FIG. 4.

Here a number of reference measurements are shown 120, as well as a number of sample measurements 121, and they have each been arranged by temperature, as denoted by the bottom axis 122. Although the reference measurements and sample measurements were not made at exactly corresponding temperatures, missing 'paired' measurements can be approximated 130, 131 using standard extrapolation, or interpolation methods.

Figure 5:
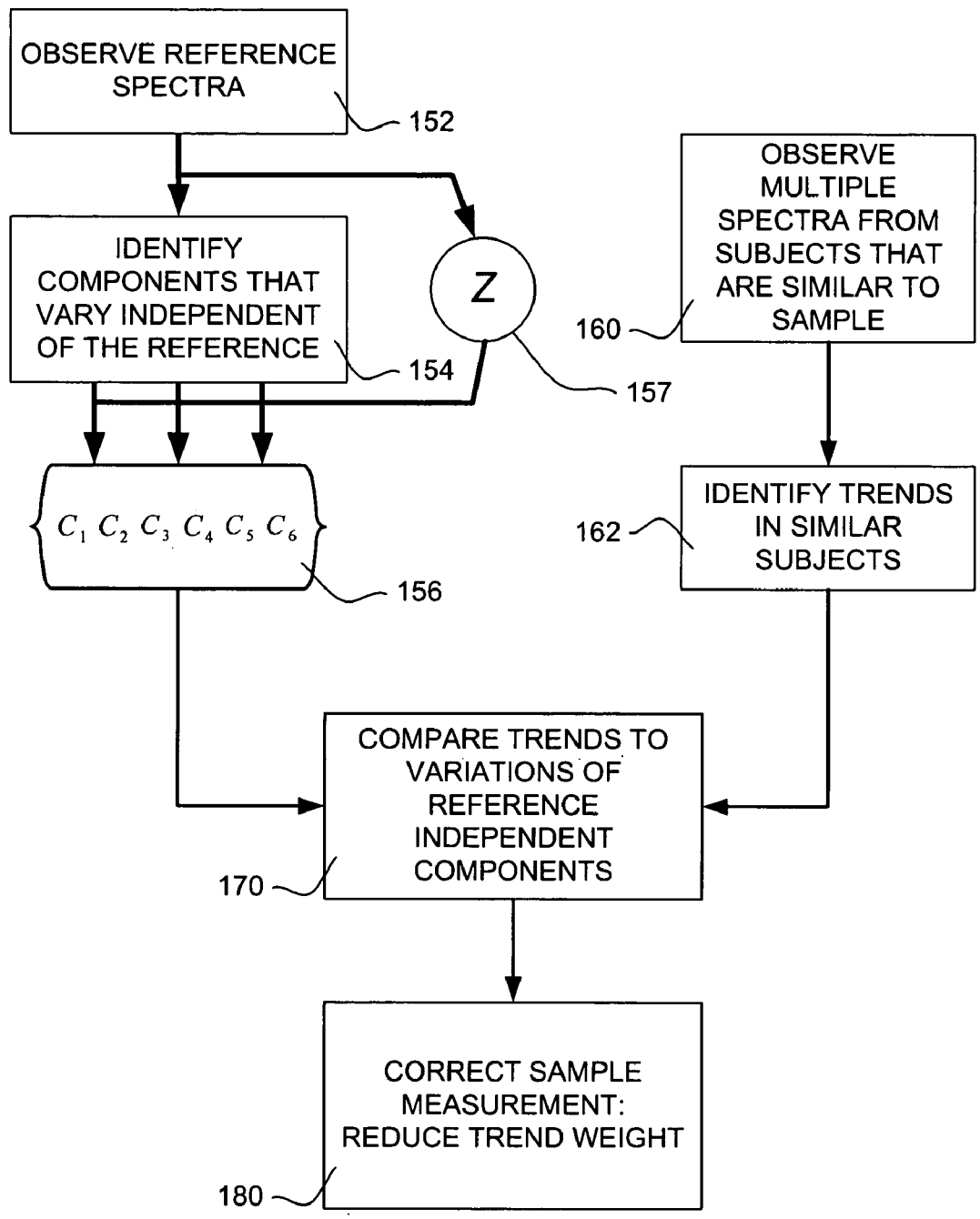
FIG. 5 is a block diagram of a process illustrating an example embodiment of the present invention.

FIG. 5 is a block diagram of a process illustrating another example embodiment of the present invention. FIG. 5 shows two separate branches of analysis. One branch has steps for identifying reference-independent varying measurement components. This process begins with observation of several reference measurements 152. This can include observation of one or more references, which might or might not be varying, under a number of different measurement conditions. For example, measurements can be taken at different temperature or humidity conditions, different times, or measurements can merely be acquired in conditions that approximate the normal operation of the measurement device. Different references can be used as well, for example, one reference that varies with humidity, temperature or some other environmental condition can be used with another reference that does not vary in a manner relating to the environmental conditions. In several embodiments, the reference(s) do not vary, or display known variations. Next, reference measurement components that vary independent of the reference are identified 154 and a collection of reference-independent varying measurement components 156 is gathered. A mapping function Z 157 that relates the reference measurements to the reference-independent varying measurement components can also be determined and stored in some embodiments.

Another branch of analysis has steps for identifying variations in components of the sample measurements. Multiple measurements from samples that are similar to the sample of interest are observed 160. For example, for an in-vivo spectroscopic measurement system, measurements of similar matter (solutions or tissue from the same or other subjects, for example) can be included as similar samples. The similar samples can also be similar in terms of their analysis or presentation. For example, if viewed on a slide, very different materials can be observed, but the overall measurements can be quite similar. In one embodiment, the sample is an optical measurement of tissue constituents in a human forearm, and the similar sample spectra are spectra captured from other optical measurements of tissue constituents in human forearms, which can be from the same or different persons.

The next step is to identify correspondences in measurement component variations in similar subjects 162 to reference-independent measurement variation components for references 156. This is achieved in a comparison step 170. With the correspondences identified, the measurement distortions in the subject measurements are calculated, and the measurement (or measurements) are corrected 180 by reducing the size of the sample measurement distortions corresponding to the reference-independent measurement components 156.

In another embodiment, rather than observing or looking for correspondences in the data captured from the similar sample spectra 160, one can, instead, create an estimate of the change in similar sample spectra by comparison of the reference-independent measurement components to the similar sample spectra. An estimated change in the sample spectra can be devised by observing the correspondence between the reference-independent measurement components and the similar sample spectra. With these relations, one can then observe the state of the reference-independent measurement components at the time of the sample measurement and infer an estimated change. The difference between the sample measurement and the estimated change then gives an estimation for a corrected actual sample measurement that is compensated for any sample measurement distortions.

A further embodiment can include classifying components of the reference measurement variation 152 into groups of so-called "reference components" that vary with the reference, "environment components" that vary with the measurement conditions (for example, humidity and temperature) and groups of "system components" that do not appear to vary with the reference and/or measurement conditions. The similar sample spectra 160 can then be observed to seek variations corresponding with the environment components, and this correspondence is used to correct or adjust sample measurements. Alternatively, the similar sample spectra 160 can be observed to find measurement component variations corresponding to system component variations, and the sample measurements can be corrected or adjusted by reducing the weight of any related variations.

Figure 6:
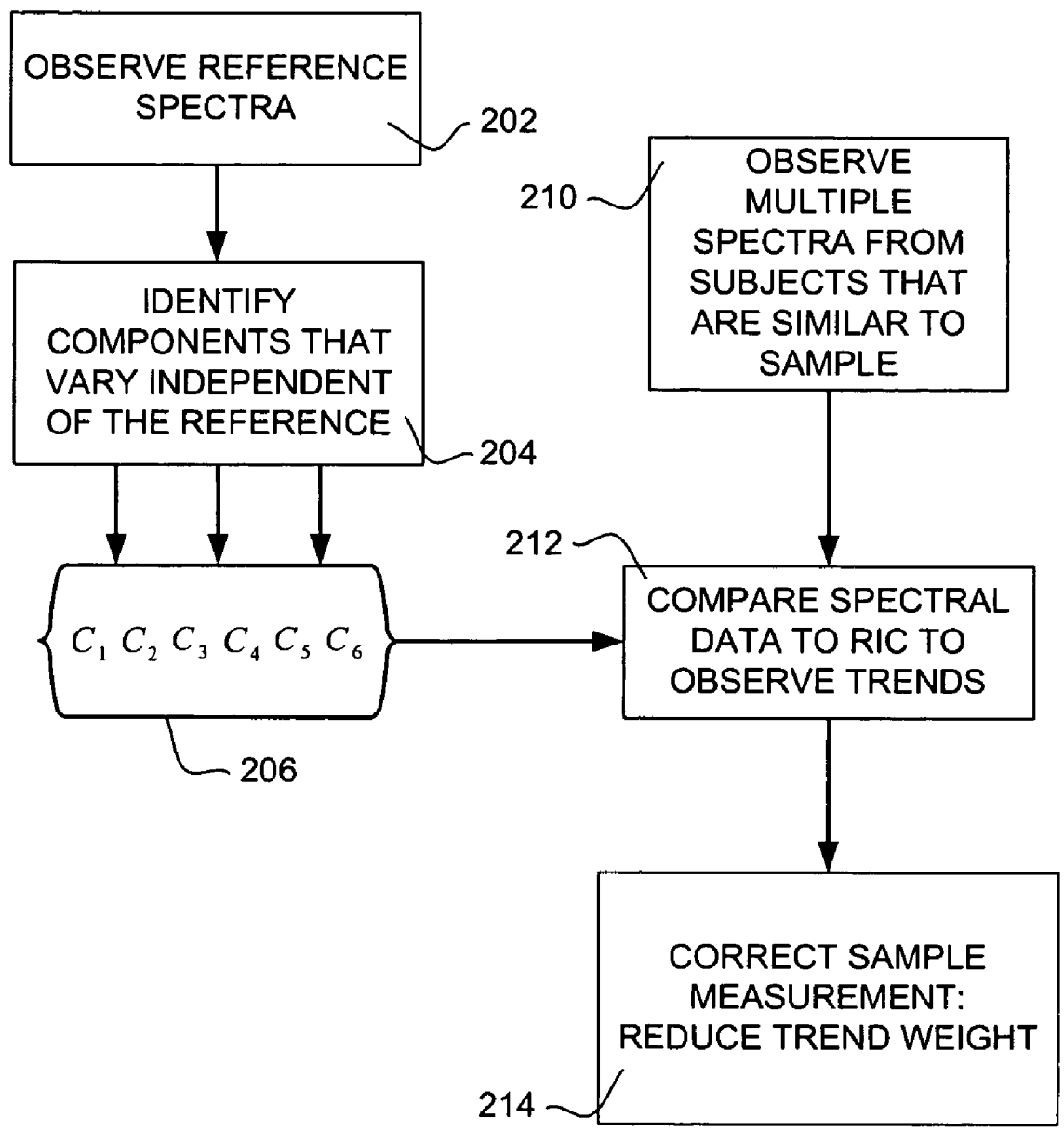
FIG. 6 is a block diagram of a process illustrating an example embodiment of the present invention.

FIG. 6 illustrates another embodiment in block diagram form. The method includes a step of observing several reference measurements 202. From the observations, reference-independent measurement components are identified 204. The reference-independent measurement components 206 can then be observed and used in the other branch of the process. In the other branch of the process, multiple measurements from samples that are similar to the sample are observed 210. The spectral measurement data from the several similar samples are compared to the reference-independent measurement components to observe corresponding variations. With corresponding variations identified the sample measurement distortions can be calculated, and adjusted for in the sample measurements if desired.

Figure 7:
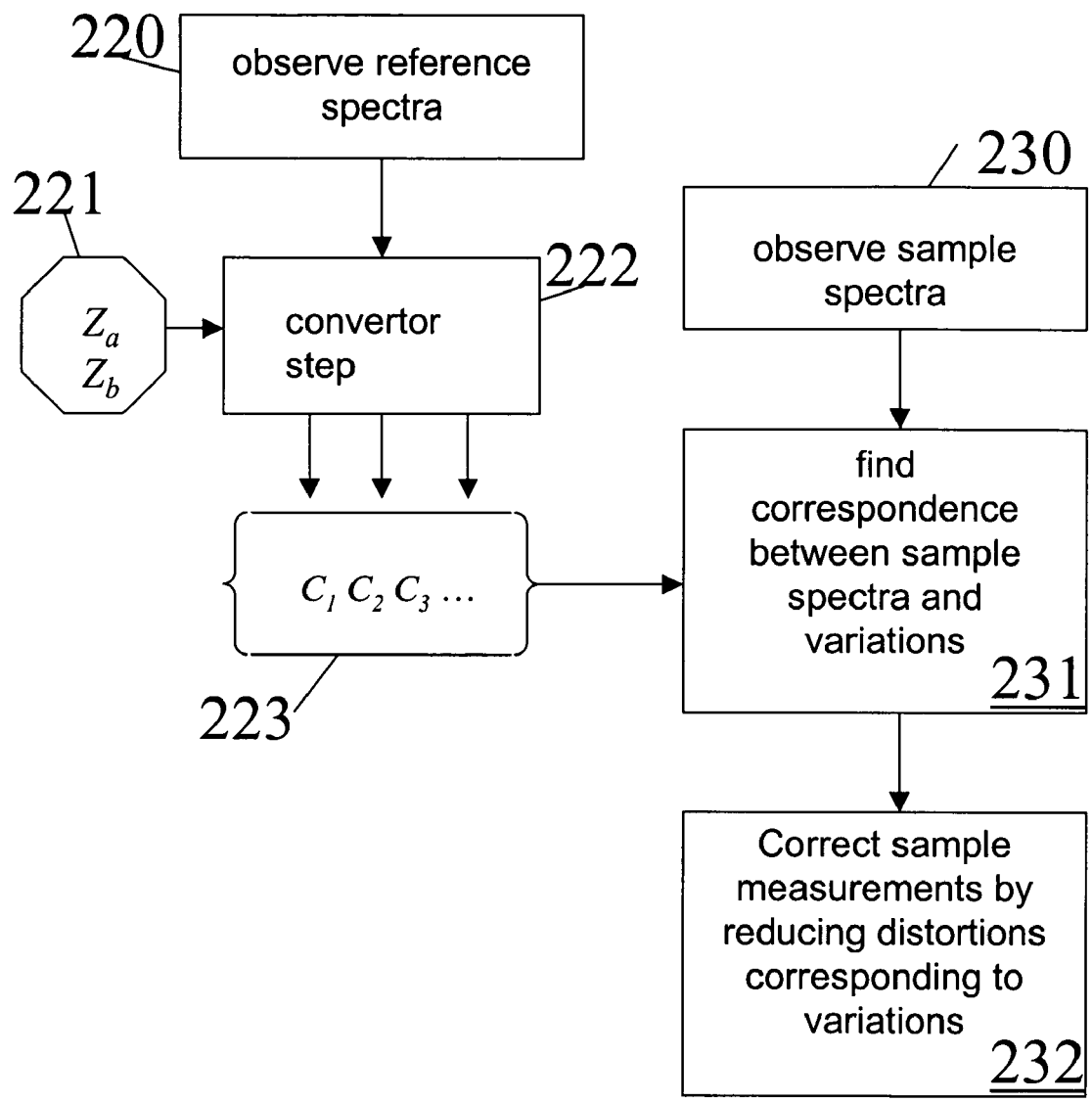
FIG. 7 is a block diagram of a process illustrating an example embodiment of the present invention.

FIG. 7 illustrates another embodiment. The method includes a step of observing several reference measurements 220, but in this embodiment a set of mapping functions 221 (Zi) have been established by empirical observation, or knowledge of measurement distortions that directly produce the reference-independent measurement components from the reference measurements 222. The reference-independent measurement components 223 can then be used in the other branch of the process. As with embodiments described above, multiple measurements from samples that are similar to the sample are observed 230. The spectral measurement variations from the several similar samples are compared to the reference-independent measurement components to determine corresponding variations. With corresponding variations identified the sample measurement distortions can be calculated, and adjusted for in the sample measurements if desired.

In one embodiment, the reference-independent measurement components 206 can be used one-at-a-time or in combinations in performing a multivariate analysis on variations observed in the multiple similar sample spectra. The reference-independent measurement component variations 206 can be used to identify variations in the similar sample spectra, rather than being used to compare to observed variations. This can be useful in complex analyses that involve large amounts of data, where variation-spotting can be difficult, if not impossible, if the variation(s) being sought are not already identified. The reference-independent measurement component variations 206 can serve as "models" in a survey seeking out related variations from the multiple similar subject spectra. Once similarities between variations in the similar subject spectra and the reference-independent measurement component variations 206 are identified, the sample can be corrected 214 by reducing the magnitude of the sample measurement component variations that correspond to the reference-independent measurement component variations 206.

The following description includes a more detailed explanation of each of the several steps of a process similar to that illustrated above in any of FIGS. 3–7. The aim is to resolve the measurement distortion, $\delta_i$, from the purported measurement in the absence of the distortion, $x_i^o$, for the ith observed measurement, $x_i$, where $x_i$ arises from the following relationship:

$$x_i = f(x_i^o, \delta_i) \tag{11}$$

The distortion has the general form:

$$\delta_i = f(q_i, S_i, t_i, e) \tag{12}$$

where q expresses the magnitude of the distortion or distortions, S expresses the functional form of the distortion or distortions on the measurement, t expresses an element of time, and e expresses effects not modelable by q and S. e may, for instance represent random events such as photon shot noise. The subscript indicates that all variables correspond to the ith measurement. If the sample measurement is vector-valued, for example in the measurement of spectra (i.e., many wavelengths are measured, or many spatial channels are read), then the values above can be vector- or even matrix-valued.

$$\delta_i = f(Q_i, S_i, t_i, E) \tag{13}$$

As a simple example, if the function expressed in equation 13 was linear in Q and S, and t did not influence the functional form of the distortions, then the modelable distortion in the ith vector measurement (which excludes e) can be represented by $$\delta_i = q_i^T \cdot S_i \tag{14}$$

If, for instance, the distortion is arising from three components of variation, then the magnitude or state of the components of variation for measurement i is given by $$q_i^T = [q_1 \ q_2 \ q_3] \tag{15}$$

and the functional vector response of the device measurement to the components of variation is given by $$S_i = \begin{bmatrix} S_{i,1}^T \\ S_{i,2}^T \\ S_{i,3}^T \end{bmatrix}$$

The variations in the distortion over a series of vector measurements entails an extension of equation 13 to $$\Delta = QS \tag{17}$$

where many $q^T$'s populate the rows of matrix Q. For this linear case, reference (or background) subtraction often fails because the functional form of the distortion in the measurement response, S, is often not equivalent across measurement platforms, samples, or even measurement conditions. For an example in in-vivo spectroscopy, the functional form of the response of the measurement to disturbances is typically very different in diffusely reflecting references (e.g., an integrating sphere) compared to human tissue due the considerable differences in optical properties (e.g., absorption, scattering). Following the logic presented above (equations 1–10), the reference and in-vivo tissue sample measurement distortions arise from $$\Delta_{ref}=QS_{ref} \quad (18)$$

$$\Delta_{tiss}=QS_{tiss} \quad (19)$$

and the following inequalities are thusly implied:

$$S_{ref} \neq kS_{tiss} \quad (20)$$

$$\Delta_{tiss} \neq k\Delta_{ref} \quad (21)$$

(Here, k is any scalar value, as in equation 6 above.) Since $S_{ref}$ and $S_{tiss}$ are not equivalent, the distortions $\Delta_{ref}$ and $\Delta_{tiss}$ are not equivalent between the reference and tissue measurements in this example, and background subtraction as it is traditionally done does not alleviate the effect of the distortion on the tissue measurement.

In an embodiment of the invention addressing the above inequalities, a search for components of variation in the sample measurement corresponding to those observed for the reference-independent measurement components of variation is undertaken. For example, the reference-independent components of variation in the reference measurements may be determined based on some previously known measurement distortion causes, e.g., source flux. If Z denotes a known mapping function of the reference measurements, $x_{ref}$, to the state of a component of measurement variation, e.g., source flux state, described by q then the components of reference-independent measurement variation can be produced directly using:

$$q=Z(x_{ref},t) \quad (22)$$

For example, if the components of the reference-independent measurement variation are linearly related to the reference measurement, the matrix B at time t may simply map the reference measurement to the components of reference-independent measurement variation:

$$q=x_{ref}^T B_t \quad (23)$$

Alternatively, if Z is not known it can be derived empirically with known components of reference-independent measurement variation. As illustrated in FIG. 4, q could also be an interpolation or extrapolation. With components of variation of source intensity states being described by many q vectors (the rows of the matrix Q), then the similarly varying measurement components of the sample measurements (X) can be reduced using the following equation:

$$\tilde{X}=(I-Q\Gamma(Q^T\Xi Q)^+Q^T\Xi)X \quad (24)$$

In equation 24 $\tilde{X}$ is the resulting adjusted sample measurements, $\Gamma$ is an adjustable matrix of weights for increasing or decreasing the measurement adjustments (with the elements of $\Gamma$ large, large adjustments are made to the sample measurements, while as $\Gamma$ tends to the zero matrix, minimal adjustments are made), and $\Xi$ is a Toeplitz matrix that is a function of the measurement components known to relate to the sample variations. If such variations are unrelated to the sample measurement distortions, then the $\Xi$ matrix is such that it tends to I, the identity matrix. X is a matrix of similar sample measurements with corresponding measurement variations to the reference-independent components of measurement variation in Q. In instances in which just a single sample measurement vector, $x_i$, is adjusted equation 24 becomes:

$$\tilde{x}_i=x_i-q_i\Gamma(Q^T\Xi Q)^+Q^T\Xi X \quad (25)$$

where $q_i$ denotes the state of a reference-independent component (or components) of measurement variation for the sample measurement $x_i$.

One skilled in the art will also realize that, in the interest of saving computational time, or storage space for the variables in equation 24 or 25, several variables can be collapsed under certain conditions for repeat usage, e.g., a single matrix H could be stored in place of the entities comprising $\Gamma(Q^T\Xi Q)^+Q^T\Xi X$, or portions thereof. This simplifies the calculation of equation 24, 25 in real time as new reference and sample measurements become available, as the equation now becomes:

$$\tilde{x}_i=x_i-q_i H \quad (26)$$

The adjustments in equation 24 and 25 above are most efficient when the sample measurement distortion, $\Delta$, can be represented as:

$$X=X^o+\Delta=X^o+QS_{samp} \quad (27)$$

When the distortions are not this straightforwardly approximated, a more general expression for the adjusted spectrum, $\tilde{x}_i$, can be used:

$$\tilde{x}_i=f(x_i,q_i,X,Q,\Gamma,\Xi,t) \quad (28)$$

The precise form of equation 28 is highly dependent on the underlying phenomena driving the distortion, and the present invention does not rely on a specific form. What remains consistent in equation 28 as with the earlier embodiments is that the reference-independent components of measurement variation, q, are used to adjust the sample measurement(s), rather than just the distortion in the reference measurements.

In some embodiments, the mapping functions Z of equation 22 can be formulated from knowledge of the system and measurement device (e.g., the responsivity profile of the detector, or the color temperature profile of the source), while in other circumstances the mapping functions can be derived empirically from observations of the reference measurements in conjunction with assessments of known reference-independent components of variation. In other embodiments, the mapping functions can be empirically derived simply by observing the reference measurements over some changing set of (unkown) conditions. With the deployment of measuring devices, it may be advantageous to deploy set mapping functions Z. In these circumstances, the details of the mapping functions (empirically or otherwise derived) can be established before shipping. However, some situations exist where the details of the mapping functions would best be determined in real-time as new information becomes available. In this situation the mapping functions can adapt in real-time to new measurement component variations of the reference or sample.

In some embodiments Z maps the reference-independent measurement components of variation to interpretable events or variations for the purposes of identifying problematic variations, or states of variation in specific components. Further, in some embodiments the states of the components of variation, q, reflect the state of the measurement environment or measurement instrument, and in such embodiments the state vector q can be used to identify conditions which are not suitable for sample measurements based on prior definitions of unsuitable measurement conditions. For example, several of the components of variation in q may relate to the state of a spectroscopic light source, such as color temperature, or flux. If it was determined through q that the source flux was insufficient to make an acceptable measurement of the sample, the measurement may be aborted, or the instrument performance adjusted to compensate.

In other embodiments, the mapping functions map the reference measurement components of variation to unknown events or variations, or combinations of variations. In this embodiment the identification of the precise cause of the variation is unimportant, and the components of variation of the reference measurements are simply used to identify corresponding measurement variations in the sample measurements. Even though the cause of the variations might be unknown, it is still feasible to identify conditions unsuitable for sample measurements, based on prior definitions of suitability. As an example of this approach, components of the reference measurement variations can be spanned using a factorization of several reference measurements. For example, multiple measurements of an inert (non-varying) reference, $X_{ref}$, can be factored using singular value decomposition as:

$$X_{ref} = UDV^T \qquad (29)$$

Columns of U, representing combinations of components of variation in the reference measurements, can be used as surrogates for the true underlying components of measurement variation distorting the sample measurements. We refer to these abstract components of variation as surrogate sensors, since they do not necessarily reflect physical components of variation present in the sample measurements, but they act as surrogates for combinations of components of measurement variation. Based on some selection criteria, e.g., fraction of variance accounted for, or correlation with environmental parameters, some or all of the columns of U may be deemed acceptable replacements for some or all columns of Q. Surrogate sensor states, $u^T$, for new reference measurements can be determined in real time from $$x_{ref}^T (DV^T)^+ = u^T \qquad (30)$$

Accordingly, selected columns of U can be substituted for Q in equation 24, 25, and $u^T$ for $q^T$.

The surrogate sensors can be used in real-time instrument operation or retrospectively in several ways. First, when a measurement instrument is operating under conditions of minimal measurement distortion, the surrogate sensors can be used to indicate that minimally distorted measurements are being taken. If this is the case, the adjustment procedure in the general equation 24 (or equations 25 or 26) will execute with very small adjustment factors in Γ. It is preferred that if no measurement distortion is indicated by the surrogate sensors, no adjustment takes place (Γ=0) as an unnecessary adjustment can contribute uncertainty to a perfectly acceptable measurement condition. Second, if a measurement instrument is operating with an unacceptable measurement distortion, and the surrogate sensor data indicates that the measurement adjustment will be dangerously large, the accuracy of inferences from the measurement or adjusted measurement can be deemed unacceptable. The measurement instrument can then be serviced, or re-calibrated by adjusting the data processing that takes place for received measurements. Third, if the measurement instrument is operating with an unacceptable measurement distortion, but the surrogate sensor data indicates that the measurement adjustment will be acceptable, then an adjustment along the lines of equation 24 or 25 takes place.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

I claim:

1. A method of correcting a measurement of a sample, comprising:
   a) determining a temporal variation of a component of several measurements of a reference, wherein the reference measurement component temporal variation does not substantially rely on changes in the reference;
   b) determining a temporal variation of components of measurements of samples that are similar to the measurement of the sample;
   c) determining whether the reference measurement temporal variation is similar to the similar sample measurement temporal variation; and, if so;
   d) adjusting the measurement of the sample by correcting for the portion of the component corresponding to the similar sample temporal variation that corresponds to the reference measurement temporal variation;
   wherein the components of measurements of samples comprise spectral data at a specific wavelength, and wherein the component of measurement of a reference does not include spectral data at the specific wavelength.

2. A method according to claim 1, wherein the component of several measurements of a reference comprises a component of several spectral measurements of a reference.

3. A method according to claim 1, wherein the component of several measurements of a reference comprises a non-spectral sensor output.

4. A method according to claim 1, wherein the component of several measurements of a reference comprises a combination of a non-spectral sensor output and a component of several spectral measurements of a reference.

5. A method according to claim 1, wherein the components of measurements of samples comprise a physical property of a sample other than its spectral response.

6. A method according to claim 1, wherein the component of several measurements of a reference comprises a physical property of the reference other than its spectral response.

7. A method according to claim 1, wherein the component of several measurements of a reference comprises a property of the measurement environment.

8. A method according to claim 1, wherein the component of several measurements of a reference comprises a measurable characteristic of spectral data.

9. A method according to claim 1, wherein the components of measurements of samples comprise a measurable characteristic of spectral data.

10. A method according to claim 1, wherein the similar samples are the sample.

11. A method according to claim 1, wherein the sample comprises human tissue.

12. A method of correcting a measurement of a sample, comprising:
   a) determining a temporal variation of a component of several measurements of a reference, wherein the reference measurement component temporal variation does not substantially rely on changes in the reference;

b) determining a temporal variation of components of measurements of samples that are similar to the measurement of the sample;

c) determining whether the reference measurement temporal variation is similar to the similar sample measurement temporal variation; and, if so;

d) adjusting the measurement of the sample by correcting for the portion of the component corresponding to the similar sample temporal variation that corresponds to the reference measurement temporal variation;

wherein the components of measurements of samples comprise combinations of spectral data at specific wavelengths, and wherein the component of measurement of a reference does not include spectral data at the specific wavelengths.

13. A method according to claim 12, wherein the component of several measurements of a reference comprises a component of several spectral measurements of a reference.

14. A method according to claim 12, wherein the component of several measurements of a reference comprises a non-spectral sensor output.

15. A method according to claim 12, wherein the component of several measurements of a reference comprises a combination of a non-spectral sensor output and a component of several spectral measurements of a reference.

16. A method according to claim 12, wherein the components of measurements of samples comprise a physical property of a sample other than its spectral response.

17. A method according to claim 12, wherein the component of several measurements of a reference comprises a physical property of the reference other than its spectral response.

18. A method according to claim 12, wherein the component of several measurements of a reference comprises a property of the measurement environment.

19. A method according to claim 12, wherein the component of several measurements of a reference comprises a measurable characteristic of spectral data.

20. A method according to claim 12, wherein the components of measurements of samples comprise a measurable characteristic of spectral data.

21. A method according to claim 12, wherein the similar samples are the sample.

22. A method according to claim 12, wherein the sample comprises human tissue.

* * * * *